(12) United States Patent
Xu et al.

(10) Patent No.: US 6,743,947 B1
(45) Date of Patent: Jun. 1, 2004

(54) ELECTROCHEMICALLY STABLE ONIUM SALTS AND ELECTROLYTES CONTAINING SUCH FOR ELECTROCHEMICAL CAPACITORS

(75) Inventors: Kang Xu, Gaithersburg, MD (US); Shengping Ding, Gaithersburg, MD (US); T. Richard Jow, Chatham, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/309,393

(22) Filed: May 10, 1999

(51) Int. Cl.$^7$ ............... C07D 213/20; C07C 311/48; C07C 211/63; C07F 38/12; C07F 9/02
(52) U.S. Cl. ............. 564/281; 564/282; 564/289; 564/82; 546/348; 361/327; 568/8; 568/74
(58) Field of Search ............. 564/291, 82, 281, 564/282, 289; 361/327; 546/348

(56) References Cited

U.S. PATENT DOCUMENTS

| | | | |
|---|---|---|---|
| 3,536,963 A | 10/1970 | Boos | 317/230 |
| 4,892,944 A | 1/1990 | Mori et al. | 544/107 |
| 5,150,283 A | 9/1992 | Yoshida et al. | 361/502 |
| 5,429,893 A | 7/1995 | Thomas | 429/218 |
| 5,527,640 A | 6/1996 | Rudge et al. | 429/213 |
| 5,568,353 A | 10/1996 | Bai et al. | 361/523 |
| 5,621,607 A | 4/1997 | Farahmandi et al. | 361/502 |
| 5,629,829 A | * 5/1997 | Ikeya | 361/505 |

* cited by examiner

Primary Examiner—Peter O'Sullivan
(74) Attorney, Agent, or Firm—U. John Biffoni; William V. Adams

(57) ABSTRACT

Based on the discovery that the melting point and solubility of onium salts are affected by the asymmetry of the substitution on cation, and that the branched substituents effectively shield onium cations from electrochemical reduction, new onium salts are synthesized and high performance electrolytes based on these salts for electrochemical capacitor are provided. The composition of the new electrolyte comprises an onium salt or mixture of such onium salts dissolved in aprotic, non-aqueous solvents or mixture of such solvents. The electrolyte is able to perform at high rate of charge/discharge, at low ambient temperatures, and within wide operating voltage, due to the high solubility, low melting temperature, and the improved reduction stability of the new onium cations, respectively.

6 Claims, 5 Drawing Sheets

ELECTROCHEMICALLY STABLE ONIUM SALTS AND ELECTROLYTES CONTAINING SUCH FOR ELECTROCHEMICAL CAPACITORS

GOVERNMENT INTEREST

The invention described herein may be manufactured, used, and/or licensed by or for the United States Government.

BACKGROUND OF THE INVENTION

1. Field of the Invention

The present invention relates generally to onium salts and to methods of producing the same. These salts, obtained by the methods provided herein, are useful components in a wide spectrum of fields, such as phase transfer catalysis, electrolyte solutes for aqueous or non-aqueous electrochemical devices, various additives, and medicaments, etc. More particularly, the present invention provides a new family of asymmetric onium cations, which when combined with an appropriate anion, result in salts having high electrochemical stability and high solubility in non-aqueous polar solvents. Most particularly, the present invention relates to the formulation of a non-aqueous electrochemically stable electrolyte solution comprising these onium salts and an appropriate solvent or solvent mixture. Finally, the present invention relates to improved electrochemical capacitors utilizing these novel electrolyte solutions and thereby having improved energy density and power capabilities.

2. Description of the Related Art

Electrochemical capacitors are energy storage devices that are able to store and release energy by the means of ion adsorption/desorption on high surface area electrodes. These capacitors typically consist of two porous electrodes that are isolated from electrical contact with each other by a separator. Both the separator and the electrodes are impregnated with an electrolytic solution, i.e., a salt or mixture of salts dissolved in appropriate solvent or mixture of solvents.

When electric potential is applied across the two electrodes during charge, ionic current flows within the capacitor due to the attraction of anions by the positive electrode and cations by the negative electrode. Upon reaching the surface of their respective electrodes, equal amounts of anions and cations are absorbed in the electrode/electrolyte interphase and are held in the region by the opposite charges in the solid electrode.

The above state of charge-separation tends to go back to the ground level of lower energy where no charge is separated. Thus, when the two electrodes are no longer held at separate potential and are connected via a load, these absorbed cations and anions desorb from the electrode/electrolyte interphase and migrate back to the bulk of the electrolyte. During this process the current produced within the capacitor drives the load as the capacitor is discharged. The above process can be repeated tens of thousands of times.

The rate at which energy can be stored/released in such capacitors is extremely high, on the order of 500~3000 W/Kg, which is higher than most electrochemical energy devices including the state-of-the-art Li-ion batteries (50~300 W/Kg). However, a disadvantage for capacitors is their low to moderate energy densities, 5~10 Wh/Kg compared to 40~200 Wh/Kg for Li-ion batteries.

The energy output (stored energy) of such capacitors is described by the following formula:

$$E = \frac{1}{2}C(\Delta V)^2 \quad (1)$$

Where E is the storable energy at a potential difference $\Delta V$ between the electrodes and C is the storage capacitance of the electrodes (B. E. Conway, *J. Electrochem. Soc.*, 1991, 138, 1539). For a given electrode material with a certain C, it is desirable to increase the operating potential $\Delta V$ in order to obtain high energy density output. However, this operating potential is always restricted by the stability limit of the solvent and salt.

For aqueous or any protic solvents, the stability limit imposed by the reduction of proton and/or oxidation of hydroxyl ion is ca. 1.2~2.0 V. Earlier efforts aimed at increased operating potential led to the use of non-aqueous aprotic solvents. See, for example, Boos et al., U.S. Pat. No. 3,536,963, and Yoshida et al., U.S. Pat. No. 5,150,283, describing electrolytes of non-aqueous solvents and ammonium salts, among others, which usually can support up to 3.0 V potential difference.

For these electrolyte solutions the stability limit is usually imposed by the decomposition of the salts, especially at the negative potential extreme, where the cation usually determines the cathodic stability limit of the electrolyte alone, independent of the anion and the solvent it is in.

Therefore it is highly desirable to find a new electrochemically stable salt, which, when dissolved in non-aqueous aprotic solvents, can provide high resistance toward oxidation and reduction. More specifically, the salt should have a cation which is stable against reduction at the negative electrode, and an anion which is stable against oxidation at positive electrode, and their stability should be higher or at least as high as that of the solvent. Thus, any improvement in electrochemical stability will increase operating potential ($\Delta V$) and have an impact on energy output by the magnitude squared as shown by Equation (1).

Furthermore, energy density can be affected by the number of ions available in the electrolytic solution (J. P. Zheng, J. Huang, T. R. Jow, *J. Electrochem. Soc.*, 1997, 144, 2026). In other words, limited solubility of most salts in aprotic, non-aqueous solvents often limits the energy density at high operating voltages. At high rate discharge/charge operations, the number of ions available in the electrolytic solution also limits the power output, i.e., where high demand for ions lowers the ion concentration in the solution thus increasing the resistance and limiting the power output. It is therefore also highly desirable to find a salt having higher solubility in aprotic, non-aqueous solvents.

The electrolyte used in state-of-the-art electrochemical capacitors contains tetraethylammonium tetrafluoroborate ($Et_4NBF_4$) in propylene carbonate (PC) solvent as described in U.S. Pat. No. 5,150,283, A. Yoshida and K. Imoto, "Electric Double Layer Capacitor and Method for Producing the Same"; or the same salt in acetonitrile (AN) solvent as described in U.S. Pat. No. 5,621,607, C. J. Farahmandi and J. M. Dispennette, "High Performance Double Layer Capacitors Including Aluminum Carbon Composite Electrodes". However, these electrolytes have serious shortcomings.

For example, the electrolyte solution of $Et_4NBF_4$ in PC exhibits low salt solubility, having a saturated concentration of 0.86 M at room temperature, and low conductivity of 8.8 mS/cm at 0.65 M at room temperature. This electrolyte is suitable for low power applications such as memory protection but not for high power applications.

In contrast, the electrolyte solution of $Et_4NBF_4$ in AN has high conductivity, about 50 mS/cm at 1.4 M at room temperature, and the saturated salt concentration is about 1.68 M at room temperatures. However, the operating voltages of the capacitor using this electrolyte is about 0.5 V lower than that using the electrolyte of $Et_4NBF_4$ in PC. Furthermore, the high vapor pressures of AN makes it unsuitable for applications at elevated temperatures.

Where both high salt solubility and high operational voltage are desired for an electrolyte, the state-of-the-art solutes comprising symmetrical quaternary ammonium salts such as tetraethyl ammonium salt are inadequate. The present invention fulfills these needs by providing asymmetrical onium salts or mixtures of such salts in aprotic, non-aqueous solvents or mixtures of such solvents. These novel electrolytes are able to perform at a high rate of charge/discharge, at low operating temperatures, and within a wide range of operating voltage due to the high solubility, low melting temperature, and the improved reduction stability of the new onium cations, respectively.

SUMMARY OF THE INVENTION

Accordingly, it is a primary object of the present invention to provide an electrochemically stable salt.

It is another object of the present invention to provide an electrochemically stable salt having electrochemically stable cations against reduction at the negative electrode, and electrochemically stable anions against oxidation at the positive electrode.

It is still another object of the present invention to provide a salt which comprises electrochemically stable onium cations, and electrochemically stable inorganic or organic anions.

It is still another object of the present invention to provide an electrochemically stable salt which also has high solubility in an aprotic, non-aqueous solvent or mixtures of such solvents.

It is still another object of the present invention to provide an electrochemically stable salt having a low melting temperature.

It is yet another object of the present invention to provide an electrolyte formulation comprising an electrochemically stable onium salt or mixture of such salts dissolved in an aprotic, non-aqueous solvent or mixture of such solvents.

It is a still further object of the present invention to provide an electrolyte capable of performing at a high rate of charge/discharge, at low ambient temperatures, and within a wide range of operating voltages.

It is a still further object of the present invention to provide an electrochemical capacitor comprising two porous electrodes, a separator, and the aforementioned electrolyte having an electrochemically stable salt solute.

In satisfaction of the foregoing objects and advantages, the present invention provides a novel family of onium salts which, in appropriate solvents, will form electrolyte solutions having these desirable properties.

The foregoing and other objects and advantages of the present invention will hereafter become more fully apparent from the following detailed description. In the description, reference is made to examples and drawings which form a part hereof, and in which is shown by way of illustration, and not limitation, preferred embodiments. Such description does not represent the full extent of the invention, but rather, the invention may be employed according to the full scope and spirit of the invention as defined in the appended claims.

DETAILED DESCRIPTION OF THE PREFERRED EMBODIMENTS

Figure 1:
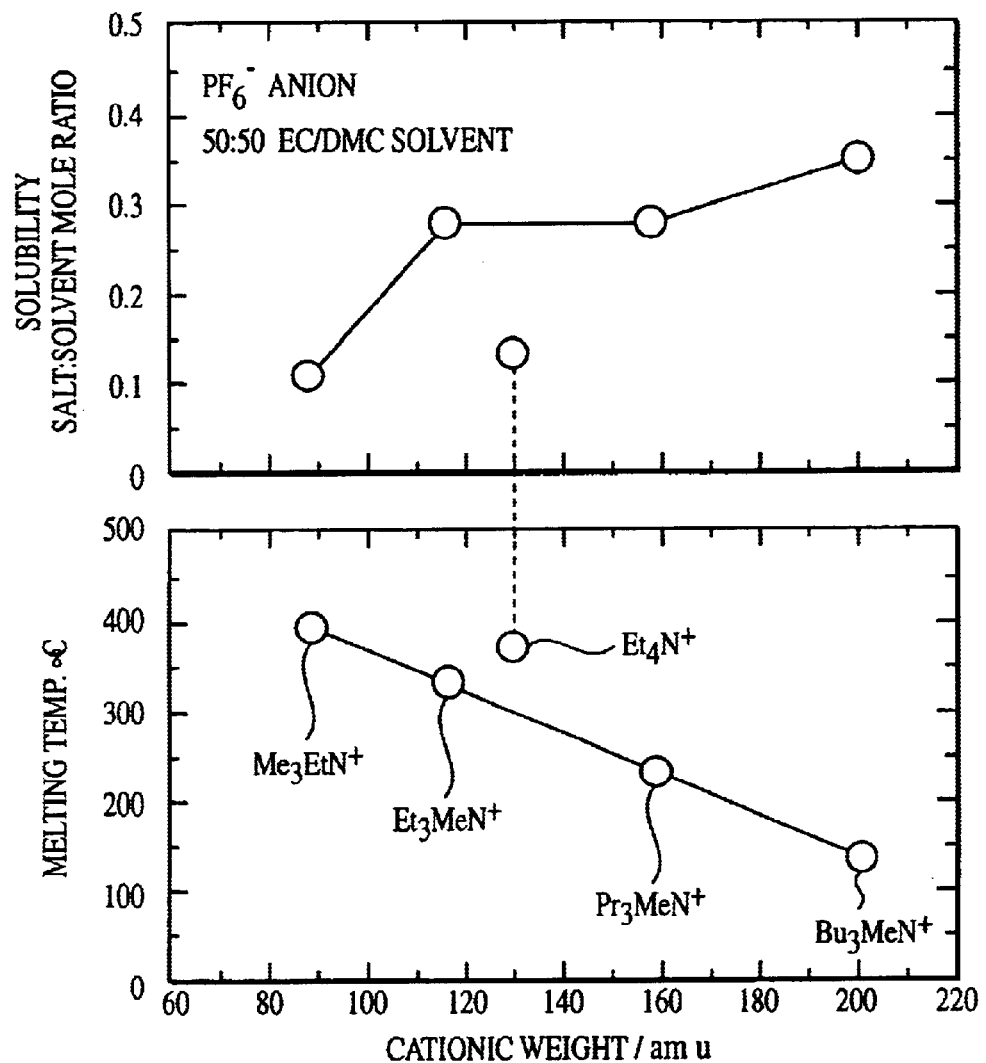
FIG. 1 shows the correlation of melting point and solubility (in 50:50 EC:DMC) with weight as well as symmetry for some of the onium cations described in the present invention. Commercially available salt tetraethylammonium hexafluorophosphate ($Et_4N^+PF_6^-$) is used as a control.

The practice of the present invention will employ, unless otherwise indicated, conventional techniques of synthetic chemistry, electrochemistry and battery/capacitor engineering that are within the skill of the art. Such techniques are explained fully in the literature. See, for example, March's *Advanced Organic Chemistry*, House's *Modern Synthetic Chemistry*, Houben-Weyl's *Methoden der organischen Chemie*, Hiers' text *Organic Synthesis*, U.S. Pat. No. 4,892, 944 to Mori et al., and Lindens' *Handbook of Batteries*.

Definitions

Before describing the present invention in detail, it is to be understood that this invention is not limited to the particular cations or salts, methods of synthesis, solvents or the like, which are described in the preferred embodiments, as such may vary. It is also to be understood that the terminology used herein is for the purpose of describing particular embodiments only, and is not intended to be limiting.

In this specification and in the claims which follow, reference will be made to a number of terms which shall be defined to have the following meanings:

The term "onium cation" is used to indicate a positively charged atom group, which is formed because the central Lewis basic atom increases its valency by donating a lone pair of electrons;

The term "substituents" is used to indicate the group of atoms which are covalently bonded to the central atom of the onium cation;

The term "normal alkyl" as used herein refers to unbranched, saturated hydrocarbon groups, such as methyl, ethyl, n-propyl, n-butyl, n-pentyl, n-octyl and the like, with preferred normal alkyl groups are unbranched alkyl group containing 1 to 10 carbon atoms;

The term "branched alkyl" as used herein refers to the group of saturated hydrocarbons which contain at least one secondary or tertiary carbon atom which are designated as "branch points", such as iso-propyl, sec-butyl, iso-butyl, tert-butyl, iso-pentyl, neo-pentyl and the like. Preferred branched alkyl groups are branched alkyl groups with a branch point close to the central atom of the onium cation, and with 3 to 8 carbon atoms;

The term "alkenyl" as used herein refers to a branched or unbranched hydrocarbon chain typically containing from 2 to 10 carbon atoms and at least one double bond;

The term "aryl" as used herein refers to a monocyclic or multiple-cyclic aromatic moiety, and is typically phenyl;

The term "arakyl" as used herein refers to moieties containing both alkyls and aromatic moieties as defined above, typically containing less than 10 carbon atoms;

The term "halogen" as used herein refers to fluoro- (hereafter designated as F), chloro- (hereafter designated as Cl), bromo- (hereafter designated as Br) or iodo- (hereafter designated as I), and usually relates to substitution for a hydrogen atom in an organic compound, this substitution is optionally a full substitution for the hydrogen;

The term "sulfone" as used herein refers to the class of compounds which are dioxides of the corresponding sulfide;

The term "ether linkage" as used herein refers to oligomeric collection of the units containing alkylene oxygen linkages, such as $(CH_2OCH_2)_n$ or $(CH_2O)_n$ where n ranges from 2 to 50;

The term "carbonic diester" as used herein refers to compounds having the structure R—O—C(O)—O—R;

The terms "asymmetry" and "asymmetrical" refers to the substituents on the onium cation, where at least one of the substituents is different from the rest;

"Optional" or "optionally" means that the subsequently described circumstance may or may not occur, and that the description includes instances in which the said circumstance occurs and instances in which it does not.

As a primary aspect of the invention, the new salts are constructed on the basis of onium cations having the structure as shown in formulas (I), (II) and (III):

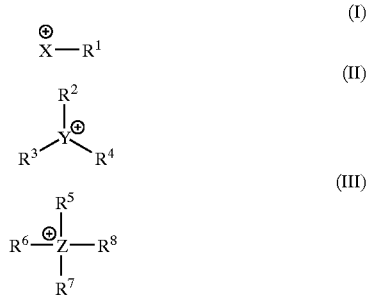

wherein X, Y and Z are central atoms bearing the charge, and are either elements selected from Groups 14, 15, 16 or 17 of The Periodic Table of the Elements or any inorganic/organic Lewis base groups, and $R^1$, $R^2$, $R^3$, $R^4$, $R^5$, $R^6$, $R^7$ and $R^8$ are substituents independently selected from the groups consisting of (a) $C_1$~$C_{10}$ normal alkyl, (b) $C_3$~$C_{10}$ branched alkyl, (c) $C_6$~$C_{12}$ aryl, (d) $C_7$~$C_{15}$ aralkyl, and (e) $C_1$~$C_{10}$ normal or branched alkyl containing functional groups, such as, but not limited to, (i) 0~2n+1 halogens, wherein n is the number of carbon atoms in the substituent, (ii) sulfone, (iii) ether linkage, and (iv) carbonic diester. Optionally, within a structure any two substituents $R^i$ (i=1~8) as defined above may link together and form a cyclic bridge.

More preferentially but not intending to be limiting, the following specifications apply to the above structures (I), (II) and (III):

That the central atom group X is selected from the following organic or inorganic compounds of Lewis base nature: heterocyclic bases such as pyridine; nitrile (R'-CN); nitroso (R'-NO); nitro (R'-NO); carbon oxide (CO); and azide (R'N$_3$); where R' is selected from the categories (a) through (e) for substituents as defined above;

That the central atom Y is preferentially, but not limited to, Oxygen, or Sulfur;

That the central atom Z is preferentially, but not limited to, Nitrogen or Phosphorus;

That $R^1$ is different in structure from the X atom group;

That at least one of the 3 substituents $R^i$ (i=2~4) in structure (II) is different from the other substituents;

That at least one of the 4 substituents $R^i$ (i=5~8) in structure (III) is different from the other substituents;

That the alkyl substituents and the functionalized alkyl substituents as defined above are preferentially branched;

That the alkyl substituents and the functionalized alkyl substituents as defined above are preferentially branched; and more preferably that the branching point be closer to the central atom of the cation as opposed to further away from the central atom;

In still further aspects of the invention, the anions of the salt are selected from the organic or inorganic anions known to those skilled in the art, among which are, but not limited to, triflate ($CF_3SO_3^-$, hereafter designated as Tf$^-$); bis(trifluoromethane sulfonyl)imide (($CF_3SO_2)_2N^-$, hereafter designated as Im$^-$); tetrafluoroborate (hereafter designated as $BF_4^-$); perchlorate (hereafter designated as $ClOF_4^-$); tris(trifluoromethanesulfonyl)methide (($CF_3SO_2)_3C^-$, hereafter designated as Me$^-$); polyhaloaluminate ($AlX_4^-$, X=F, Cl, Br and I); bis(penta fluoroethane sulfonyl)imide (($C_2F_5SO_2)_2N^-$); hexafluoroarsenate (hereafter designated as AsF6$^-$); and hexafluorophosphate (hereafter designated as PF$_6^-$); and the mixtures thereof.

In yet further aspects of the invention the new salts based on the above-defined cations and anions are dissolved in an aprotic, non-aqueous solvent or the mixture of such solvents known to those skilled in the art, among which are, but not limited to, cyclic carbonates including ethylene carbonates (hereafter designated as EC), propylene carbonates (PC) etc, linear carbonates including dimethyl carbonate (DMC), diethyl carbonate (DEC), ethylmethyl carbonate (EMC) etc, and sulfones including ethylmethylsulfone (EMSF), sulfolane, dimethylsulfone etc., thereby forming improved electrolyte solutions.

Experimental

Materials

All chemicals used in the synthesis were used as received. All solvents used in the fabrication of electrolytes were dried and re-distilled. Activated carbon (M series) was from Osaka Gas and used without further treatment. Procedures handling the electrolytes and subsequent measurement were all conducted in a Vacuum Atmosphere Glove Box under Ar atmosphere with $O_2$ level <5 ppm and the $H_2O$ level <2 ppm.

Melting Point

Differential Scanning Calorimetry was employed to determine the melting point of the salts. Typically the experiment was conducted under a helium atmosphere at a heating rate of 5° C. The onset point of the melting process was taken as the melting point.

Electrical Conductivity

Impedance spectroscopy was employed to determine the solution bulk resistance and conductivity was then derived from the cell geometry, which comprised a pair of parallel platinum electrodes. The cell was placed in a temperature-controlled environment and computers were used to control the heating/cooling as well as impedance measurement.

Cyclic Voltammetry

Electrochemical stability window was measured by cyclic voltammetry using EG&G 273 Potentiostat/Galvanostat. A three-electrode configuration cell was employed, with glassy carbon as the working electrode, Li as the reference electrode and Pt or Ti as the counter electrode. Typically a scan rate was 5 mV/s and 100 $\mu A/cm^2$ was used as cutoff current density for stability window limit.

Cell Testing

The assembled cell was subjected to charge/discharge test on an EG&G 273 Potentiostat/Galvanostat. Typically a charge/discharge rate of 1.0 $mA/cm^2$ was used.

The following examples are intended to provide those of ordinary skill in the art with a complete disclosure and description of how to make and use the novel new electrochemically stable salts in a new electrolyte formulation, and are not intended to be limiting in any way. Efforts have been made to ensure accuracy with respect to numbers used (e.g., amounts, temperatures, etc), but some deviation should be allowed for. Unless otherwise indicated, parts are by weight, and temperatures are in degrees centigrade, and pressure is near atmospheric. All chemicals, reagents and the like, are commercially available or are otherwise readily synthesized using conventional techniques well known in the art.

EXAMPLE 1

Synthesis of Ethylmethyldi(iso-propyl)ammonium Hexafluorophosphate ($EtMeiPr_2N^+PF_6^-$)

In a 500 mL flask equipped with an addition funnel, a refluxing condenser, and a stirrer, were filled 25.6 g of formic acid (0.5 mol, Aldrich, 95%) and 30.4 g di(iso-propyl)amine (0.30 mol, Aldrich, 99.5%). Under cooling and stirring was slowly added 13.0 g acetaldehyde solution (ca. 0.30 mol, Aldrich, 99%). After the solution became cleared, the reaction mixture was brought to ca. 90~110° C. in an oil bath. A vigorous evolution of $CO_2$ began after 2~3 min., during which time the flask was removed from the bath from time to time until the evolution subsided. After 30 min. the reaction mixture stabilized and was kept in the oil bath at 100° C. for 8 hrs.

After the solution cooled, 80 mL of 4.0 N HCl was added and the solution is evaporated to dryness under reduced pressure. The remaining residue was dissolved in water and the organic phase was liberated by the addition of 50 mL 9.0 N NaOH solution. The organic phase was separated and dried with anhydrous $K_2CO_3$. Distillation yielded ca. 32.0 g Ethyldi(iso-propyl)amine.

The above amine was mixed with 22.5 g dimethylcarbonate (0.25 mol, Aldrich, 99%) in 100 mL methanol. The mixture was then added to a Parr mini-reactor and the temperature was brought up to 130° C. for 5 hrs. under vehement stirring. After the reaction the product was transferred into a flask and evaporated under reduced pressure. The brownish residue, ethylmethyldi(iso-propyl)ammonium methylcarbonate ($EtMeiPr_2NMeCO_3$) weighed ca. 50.0 g.

$EtMeiPr_2NMeCO_3$ was dissolved in distilled water, and 60% hexafluorophosphoric acid ($HPF_6$) was added to this solution with precaution. After neutralization, the solution was subject to evaporation under reduced pressure to remove water. Resultant crystal was repeatedly recrystallized from hot methanol solution, and the final product $EtMeiPr_2NPF_6$ was fine needle.

EXAMPLE 2

Synthesis of Ethylmethyldi(iso-propyl)ammonium bis(Trifluoromethane sulfonyl)imide ($EtMeiPr_2N^+Im^-$)

40 g Lithium bis(trifluoromethane sulfonyl)imide (0.14 mol, 99%, 3M) was dissolved in 200 mL distilled water and was passed through a pre-protonated cation exchange column of 4.5 eq. Capacity. The collected acid solution was once again passed through the regenerated cation exchange column to ensure quantitative conversion. The resultant aqueous solution of bis(trifluoromethane sulfonyl)imidic acid was condensed to ca. 2.0 M by evaporating excess water.

The aqueous solution of bis(trifluoromethane sulfonyl) imidic acid was added to solution of $EtMeiPr_2NMeCO_3$. After the neutralization the solution was subject to evaporation under reduced pressure to remove water. Resultant solid was repeatedly recrystallized from hot methanol solution, and the final product $EtMeiPr_2N^+Im^-$ is fine needle crystal.

EXAMPLE 3

Synthesis of Ethylmethyldi(iso-propyl)ammonium Triflate ($EtMeiPr_2N^+Tf$)

Triflic acid aqueous solution was prepared in a procedure similar to that described in Example 2, except that lithium triflate (96% Aldrich) was used in the place of lithium imide, and it was then used to neutralize the solution of $EtMeiPr_2NMeCO_3$. After the neutralization the solution was subject to evaporation under reduced pressure to remove water. Resultant solid was repeatedly re-crystallized from hot methanol solution, and the final product $EtMeiPr_2N^+Tf$ obtained is fine crystal.

EXAMPLE 4

Synthesis of tri(iso-Butyl)methyl ammonium Hexafluorophosphate ($iBu_3MeN^+PF_6^-$)

40.0 g tri(iso-Butyl)amine (0.21 mol, Aldrich, 98%) and 30.0 g methyliodide (0.21 mol, Aldrich, 99%) in 200 mL alcohol were charged into a Parr mini-reactor. The reaction temperature was kept at 60° C. for 5 hrs. before the reactor was opened. With the solvent evaporated under reduced pressure, the remaining solid residue was dissolved in water and passed through a strong base (in $OH^-$ form) anion exchange column with 4.0 eq. capacity. The resultant basic solution was passed through the regenerated column again to ensure complete conversion.

After condensation, the basic solution was neutralized with $HPF_6$ and then the solution was subject to evaporation under reduced pressure to remove water. Resultant solid was repeatedly re-crystallized from hot methanol solution, and the final product $iBu_3MeN^+PF_6^+$ obtained is fine crystal.

EXAMPLE 5

Synthesis of tri(iso-Propyl)methylammonium Hexafluorophosphate ($iPr_3MeN^+PF_6^-$)

40 g di(isopropyl)amine (0.40 mol, Aldrich, 99.5%) in 100 mL of methanol was mixed with 51.2 g of formic acid (1.0 mol, Aldrich, 95%) in a 500 mL flask. Then under cooling and stirring was slowly added 33 g formaldehyde solution (ca. 0.40 mol, Aldrich, 37%). After the solution became cleared, the reaction mixture was brought to ca. 90~110° C. in an oil bath. A vigorous evolution of $CO_2$ began after 2~3 min., during which time the flask was removed from the bath from time to time until the evolution subsided. After 30 min. the reaction mixture stabilized and was kept in the oil bath at 100° C. for 8 hrs.

After the solution cooled, 100 mL of 4.0 N HCl was added and the solution is evaporated to dryness under reduced pressure. The remaining residue was dissolved in water and the organic phase was liberated by the addition of 80 mL 9.0 N NaOH solution. The organic phase was separated and dried with anhydrous $K_2CO_3$. Distillation yielded ca. 34.0 g methyldi(iso-propyl)amine.

37.0 g 2-Bromopropane (0.30 mol, Aldrich, 99%) was added slowly to methyldi(iso-propyl)amine as obtained above. The reaction mixture was kept at room temperature overnight under stirring. The crystal that formed was filtered and washed by methanol. The procedures for converting the crystal, which is methyltri(iso-propyl)ammonium bromide, into the corresponding hydroxide by anion exchange column, the subsequent neutralization with $HPF_6$ and re-crystallization in methanol were described in Example 4. The resultant $iPr_3MeNPF_6$ is fine crystal.

EXAMPLE 6

Synthesis of Methyltripropylammonium Hexafluorophosphate ($Pr_3MeN^+PF_6^-$)

In a Parr mini-reactor were charged 28.6 g tripropylamine (0.2 mol, Aldrich, 99%) and 18.0 g dimethylcarbonate (0.2 mol, Aldrich, 99%) in 200 mL methanol. The reaction mixture was kept at 120° C. overnight, and the solvent and unreacted carbonate or amine were removed through evaporation under reduced pressure.

The brownish residue, $Pr_3MeN^+MeCO_3^-$ was dissolved in distilled water, and neutralization was carried out with $HPF_6$. The subsequent re-crystallization procedure was described in Example 3.

EXAMPLE 7

Synthesis of Methyltripropylammonium Tetrafluoroborate ($Pr_3MeN^+BF_4^-$)

Tetrafluoroboric acid (Aldrich, 48% aqueous solution) was used to neutralize $Pr_3MeN^+MeCO_3^-$, the preparation of which has been described in Example 6. The subsequent re-crystallization procedure was described in example 3.

EXAMPLE 8

Synthesis of Ethyldimethylsulfonium Hexafluorophosphate ($EtMe_2S^+PF_6^-$)

15 g Ethylmethyl sulfide (0.20 mol, Aldrich, 99%) was slowly added to 100 mL methyliodide solution in t-butyl methyl ether (0.20 mol, Aldrich, 2.0 M), and the reactants were kept at room temperature overnight. The crystalline precipitate was collected by filtration, washed by diethylether, and then dissolved in distilled water.

The procedures for converting the crystal, which is ethyldimethylsulfonium iodide, into the corresponding hydroxide by anion exchange column, the subsequent neutralization with $HPF_6$ and re-crystallization in methanol were described in Example 4. The resultant $EtMe_2SPF_6$ is fine white crystal.

EXAMPLE 9

Synthesis of Triethylmethylammonium Hexafluorophosphate ($Et_3MeN^+PF_6^-$)

The synthesis of $Et_3MeN^+MeCO_3^-$ and its conversion into $Et_3MeN^+PF_6^-$ by means of anion exchange were conducted in a manner similar to that described in Example 6, except that an appropriate amount of triethylamine was used in place of tripropylamine. The resultant $Et_3MeN^+PF_6^-$ is fine crystal.

EXAMPLE 10

Synthesis of Triethylmethylammonium bis (Trifluoromethane sulfonyl)imide ($Et_3MeN^+Im^-$)

Using 2.0 M aqueous solution of bis(trifluoromethane sulfonyl)imidic acid, whose preparation was described in Example 2, aqueous solution of $Et_3MeN^+MeCO_3^-$ was neutralized. After the neutralization the solution was subject to evaporation under reduced pressure to remove water. Resultant solid was repeatedly recrystallized from hot methanol solution, and the final product $Et_3MeN^+Im^-$ is fine flake crystal.

EXAMPLE 11

Synthesis of Triethylmethylammonium Triflate ($Et_3MeN^+Tf$)

Using 2.0 M aqueous solution of triflic acid, whose preparation was described in Example 3, an aqueous solution of $Et_3MeN^+MeCO_3^-$ was neutralized. After the neutralization the solution was subject to evaporation under reduced pressure to remove water. Resultant solid was repeatedly recrystallized from hot methanol solution, and the final product $Et_3MeN^+Tf$ is fine needle crystal.

EXAMPLE 12

Synthesis of Triethylmethylphosphonium Hexafluorophosphate ($Et_3MeP^+PF_6^-$)

The synthesis of $Et_3MeP^+MeCO_3^-$ and its conversion into $Et_3MeP^+PF_6^-$ by means of anion exchange were conducted in a manner similar to that described in Example 6, except that an appropriate amount of triethylphosphine was used in place of tripropylamine. The resultant $Et_3MeP^+PF_6^-$ is fine crystal.

EXAMPLE 13

Synthesis of Tributylmethylphosphonium Hexafluorophosphate ($Bu_3MeP^+PF_6^-$)

The synthesis of $Bu_3MeP^+MeCO_3^-$ and its conversion into $Bu_3MeP^+PF_6^-$ by means of anion exchange were conducted in a manner similar to that described in Example 6, except that an appropriate amount of tributylphosphine was used in place of tripropylamine. The resultant $Et_3MeP^+PF_6^-$ is fine crystal.

EXAMPLE 14

Synthesis of 1-Methyl Pyridinium Hexafluorophosphate ($C_6H_8N^+PF_6^-$)

Equimolar pyridine and methyliodide are reacted at room temperature for two hours. The precipitate (1-methyl pyridinium iodide, $C_6H_8N^+I^-$) was filtered, and an anion exchange column was used to convert it into 1-methyl pyridinium hydroxide ($C_6H_8N^+OH^-$). Neutralization with $HPF_6$, as described in Example 4, converts the salt into pyridinium hexafluorophosphate ($C_6H_8N^+PF_6^-$), and re-crystallization was conducted in hot methanol three times. The final product is a white needle-like crystal.

EXAMPLE 15

Fabrication and Evaluation of Novel Electrolyte Containing New Onium Salts

This example describes the preparation and characterization of novel electrolytic solutions comprising the electrochemically stable onium salts whose synthesis has been disclosed in Examples 1 through 12 and appropriate solvents.

The novel electrolyte was prepared to have the following composition: one onium salt or mixtures of two or more of the onium salts as described in Examples 1 through 12, and a 50:50 mixture of ethylene carbonate (EC) and dimethylcarbonate (DMC). The amount of onium salt or mixture of onium salts were such that the total concentration was between 0.5~2.5 M, with the preferred concentration between 0.7~1.5 M.

FIG. 1 shows the correlation of melting point and solubility in 50:50 EC:DMC with cationic weight as well as the effect of cationic symmetry for some of the onium cations described in the present invention. Commercially available salt $Et_4NPF_6$ is used as control. These results confirmed that the "asymmetry" of the substitution on cation plays a decisive role in determining the melting point as well as the solubility of the salts. These asymmetrical salts described herein are much lower melting and more soluble in the aprotic solvent mixture than the symmetrical $Et_4NPF_6$. That provides the capacitors containing these asymmetrical salts with improved low temperature performance and also better high rate performance.

Figure 2:
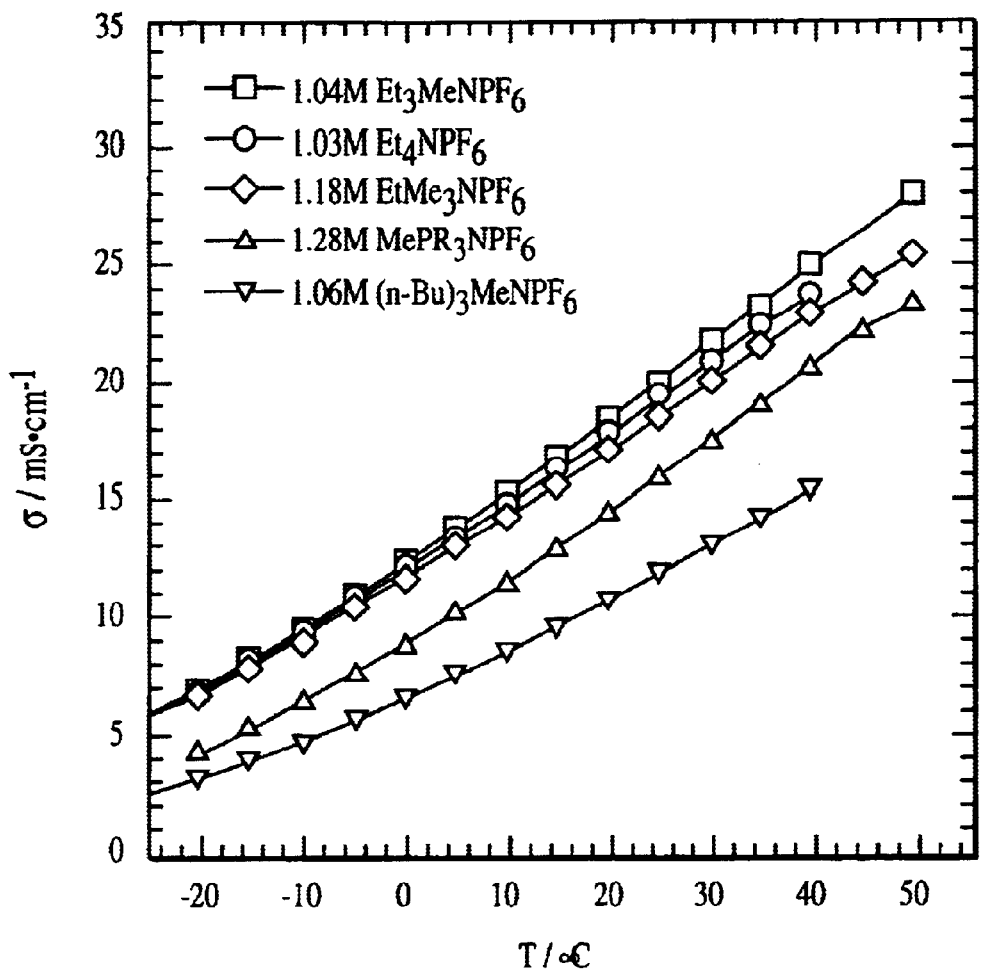
FIG. 2 shows the temperature dependence of conductivity of electrolytes comprising some of the onium salts described in the present invention. Commercially available salt $Et_4N^+PF_6^-$ is used as a control. The solvent is a mixture of EC:DMC in a 1:1 weight ratio.

FIG. 2 shows the temperature dependence of conductivity of electrolytes comprising some of the onium salts in 50:50 EC:DMC solvent described in the present invention. Commercially available salt $Et_4NPF_6$ is used as control. It can be seen that most of the asymmetrical onium salts described herein can yield conductivity higher than 10 mS/cm at room temperature.

Figure 3:
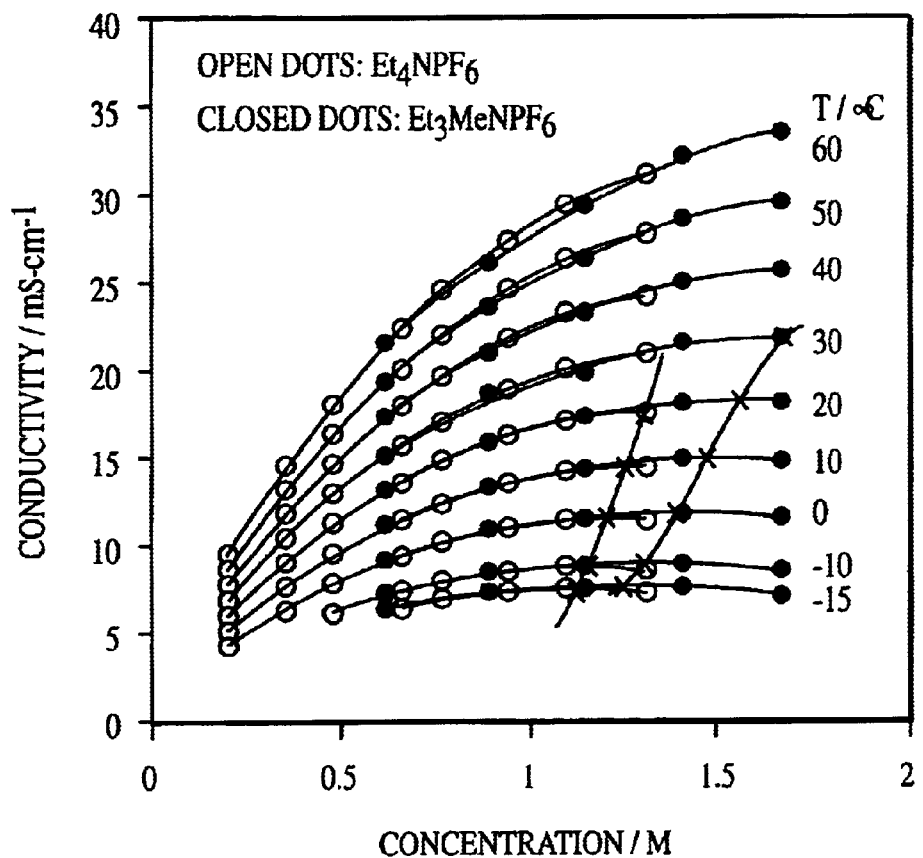
FIG. 3 shows the concentration dependence of conductivity of electrolytes based on one of the onium salts described in the present invention. Commercially available salt $Et_4N^+PF_6^-$ is used as a control. The solvent is a mixture of EC:DMC in a 1:1 weight ratio.

FIG. 3 shows the comparison of concentration dependencies between one of the onium salts in 50:50 EC:DMC as described in the present invention and the commercially available salt $Et_4NPF_6$ in 50:50 EC:DMC. Obviously, asymmetrical onium salts have maximum conductivity at higher concentration. Since high concentration minimizes the concentration polarization during charging, the novel onium salts described herein provides capacitors containing them with an advantage of working at higher rates.

Figure 4:
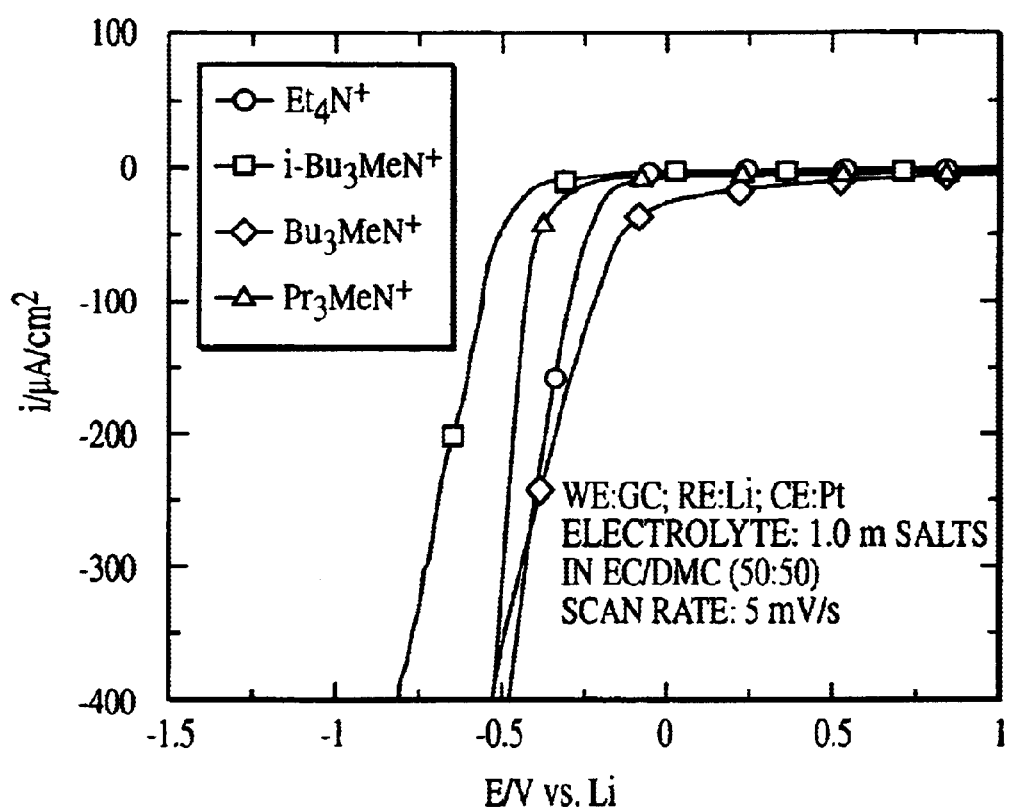
FIG. 4 shows the electrochemical stability window of the electrolyte comprising novel onium salts described in this invention, and commercially available salt $Et_4N^+PF_6^-$ is used as a control.

FIG. 4 shows the electrochemical stability window of the electrolyte comprising novel onium salts in 50:50 EC:DMC as described herein, and commercially available salt $Et_4NPF_6$ in 50:50 EC:DMC used as a control. Obviously, the asymmetrical onium cations with bulky, branched alkyl substituents tend to be reduced at much lower potential. This shielding effect of the substituents extends the electrochemical stability window by as much as 0.5 V in the case of $Pr_3MeN^+PF_6^-$ and $iBu_3MeN^+PF_6^-$. As a result, the operating voltage of the capacitor containing these novel salts described herein can be increased from 2.3~2.5 V to 2.8~3.0 V, which translates into an increase of 44% in energy density.

EXAMPLE 16

Fabrication of Electrochemical Capacitor Containing the Novel Electrolyte

This example describes the preparation of a capacitor comprising two activated carbon-based electrodes, a separator, and an electrolyte containing the novel onium salts as described in Examples 1 through 13.

The carbon electrode was prepared from 95 parts of activated carbon of various brands and 5 parts of Teflon® as binder. The resultant mixture was dispersed thoroughly in an appropriate solvent. Then the solution was either evaporated to make an activated carbon-based paste, or directly coated onto an Aluminum substrate by spraying. Typically the electrodes were cut into an area of ca. 100 $cm^2$, with loading of ca. 2.8 mg/$cm^2$. The prepared electrodes were thoroughly dried under vacuum.

Different commercial separators including Celgard® series films were used as separator.

After vigorous drying at 120° C. under vacuum the electrodes and the separator were vacuum-soaked with an electrolyte as prepared in Example 13, and were assembled as an experimental capacitor cell.

Figure 5:
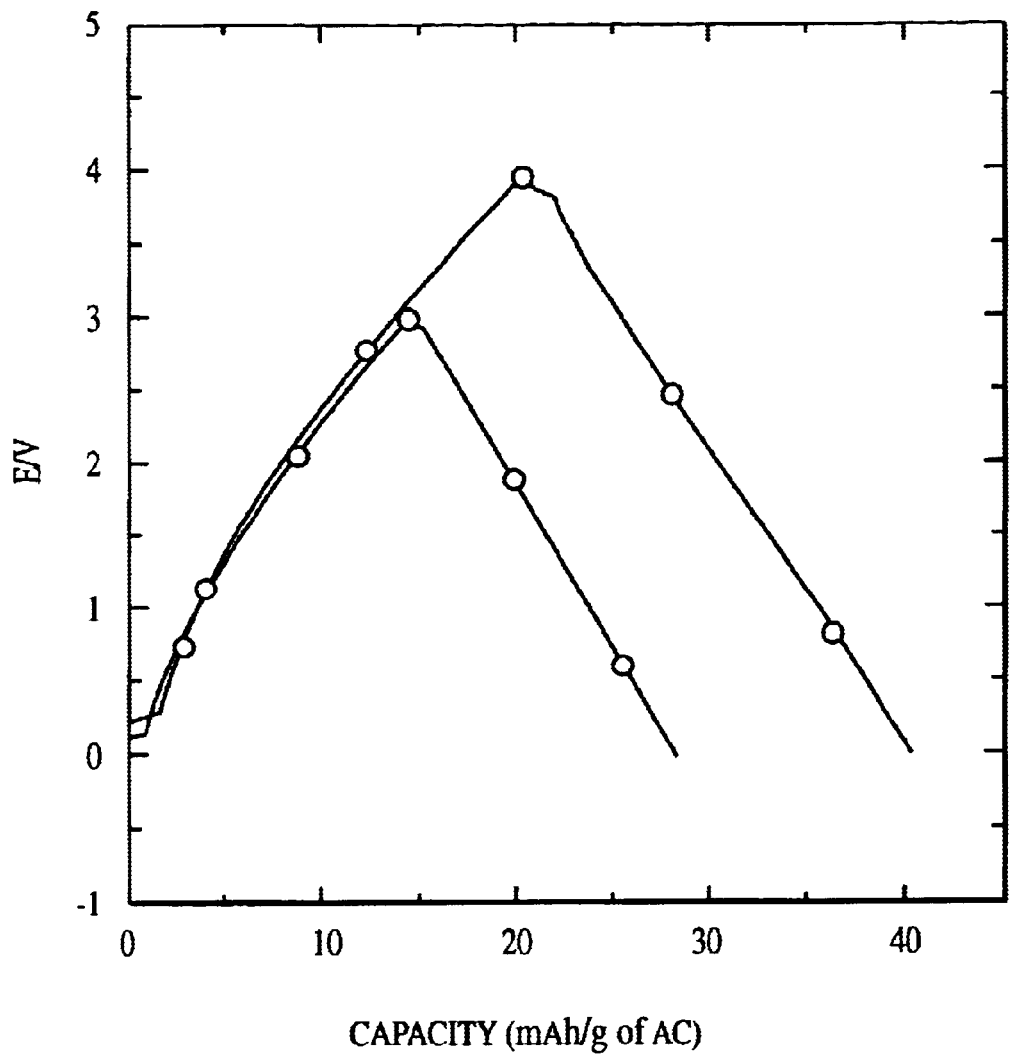
FIG. 5 shows the voltage profile for galvanostatic charging/discharging of a capacitor comprising novel electrolytes described in this invention.

FIG. 5 shows the voltage profile for galvanostatic charging/discharging such a capacitor including the novel electrolyte described herein. The charge/discharge were carried at different operating voltages, and eventually the voltage was deliberately brought over the decomposition potential of the electrolytes. While commercial capacitor (GoldCap®) burst the safety valve at ca. 4.0 V charging, the electrolytes used in this invention operate well at 4.0 V, and only failed but did not burst even at 5.0 V in a cell with the same safety valve.

While the invention has been described in detail and with reference to specific embodiments thereof, it will be apparent to one skilled in the art that various changes, alterations, and modifications can be made without departing from the spirit and scope of the invention and its equivalents as defined in the appended claims.

What is claimed is:

1. An electrochemical capacitor, comprising a pair of high surface area electrodes, a separator, and an electrolyte, wherein said electrolyte comprises an asymmetric onium salt further comprising an onium cation and an anion, and wherein said onium cation is selected from an onium cation having the structure (III):

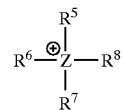

wherein Z is a nitrogen atom bearing the charge and $R^5$, $R^6$, $R^7$ and $R^8$ are selected from the groups consisting of (a) $C_1$~$C_{10}$ normal alkyl, (b) $C_3$~$C_{10}$ branched alkyl, (c) $C_6$~$C_{12}$ aryl, (d) $C_7$~$C_{15}$ aralkyl, and (e) $C_1$~$C_{10}$ normal or branched alkyls having functional groups selected from the groups consisting of (i) 0~2n+1 halogens, wherein n is the number of carbon atoms in the substituent, (ii) sulfone, (iii) ether linkage, and (iv) carbonic diester; and wherein said anion comprises an organic or inorganic anion which is selected from the group consisting of polyhaloaluminate ($AlX_4^-$, X=F, Cl, Br and I), triflate ($CF_3SO_3^-$, $Tf^-$), bis (trifluoromethane sulfonyl)imide (($CF_3SO_2$)$_2N^-$, $Im^-$, bis (penta fluoroethane sulfonyl)imide (($C_2F_5SO_2)_2N^-$), perchlorate ($ClO_4^-$), tetrafluoroborate ($BF_4^-$), tris(trifluoromethanesulfonyl)methide (($CF_3SO_2)_3C^-$, $Me^-$), hexafluoroarsenate ($AsF_6^-$), hexafluorophosphate ($PF_6^-$), and mixtures thereof;

or a mixture of such salts dissolved in an aprotic, non-aqueous solvent or mixture of such solvents.

2. The capacitor of claim 1, wherein at least one of the alkyl substituents $R^5$, $R^6$, $R^7$ and $R^8$ in structure (III) is different from the other remaining substituents in structure (III).

3. The capacitor of claim 1, wherein at least one of the alkyl substituents $R^5$, $R^6$, $R^7$ and $R^8$ in structure (III) is different from the other remaining substituents in structure (III), and at least two of the substituents $R^5$, $R^6$, $R^7$ and $R^8$ are selected from the group consisting of bulky, branched alkyl substituents.

4. The capacitor in claim 1, wherein said electrolytic solvent is selected from the group of non-aqueous, aprotic organic compounds consisting of acetonitrile (AN), adiponitrile (ADN), butylene carbonate (BC), γ-butyrolactone (γBL), diethylcarbonate (DEC), dimethylcarbonate (DMC), ethylmethylcarbonate (EMC), methyl-iso-propylcarbonate (MiPC), ethylene carbonate (EC), propylene carbonate (PC), fluoroethylene carbonate (FEC), difluoroethylene carbonate ($F_2EC$), perfluoroethylene carbonate ($F_4EC$), fluoropropylene carbonate (FPC), perfluoropropylene carbonate ($F_4PC$), dialkylsulfoxide (R—SO—R'), dialkylsofone (R—$SO_2$—R'), sulfolane, alkylsulfite (R—S(O)—OR'), α-disulfones (R—$S_2O_4$—R'), trialkylphosphate, phosphite and aldehyde.

5. The capacitor of claim 4, wherein the electrolytic solvent is a mixture of two or more of the solvents of claim 4.

6. The capacitor of claim 1, wherein the said high surface area electrodes are made of a material selected from the group consisting of carbon black, activated carbons, metal nitrides, metal carbides and conducting polymers.

* * * * *